(12) United States Patent
Petersen et al.

(10) Patent No.: US 9,733,176 B2
(45) Date of Patent: Aug. 15, 2017

(54) OPTICAL DETECTOR SCATTER CAP ASSEMBLY HAVING A REMOVABLE SCATTER BAR AND METHODS OF USING THE SAME

(71) Applicant: Becton, Dickinson and Company, Franklin Lakes, NJ (US)

(72) Inventors: Timothy Wayne Petersen, Seattle, WA (US); Veronica Lauren Kersten, Seattle, WA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 15/175,862

(22) Filed: Jun. 7, 2016

(65) Prior Publication Data
US 2016/0370294 A1  Dec. 22, 2016

Related U.S. Application Data

(60) Provisional application No. 62/181,092, filed on Jun. 17, 2015.

(51) Int. Cl.
G01N 15/14 (2006.01)
G01N 15/10 (2006.01)

(52) U.S. Cl.
CPC ..... *G01N 15/1434* (2013.01); *G01N 15/1459* (2013.01); *G01N 2015/1006* (2013.01)

(58) Field of Classification Search
CPC ........... G01N 15/1434; G01N 15/1459; G01N 2015/1006; G02B 6/4206
See application file for complete search history.

(56) References Cited

U.S. PATENT DOCUMENTS

| | | |
|---|---|---|
| 3,960,449 A | 6/1976 | Carleton et al. |
| 4,233,619 A | 11/1980 | Webb et al. |
| 4,347,935 A | 9/1982 | Merrill |
| 4,612,555 A | 9/1986 | Hongou et al. |
| 4,667,830 A | 5/1987 | Nozaki, Jr. et al. |
| 4,668,860 A | 5/1987 | Anthon |
| 4,704,891 A | 11/1987 | Recktenwald et al. |
| 4,770,992 A | 9/1988 | Van Den Engh et al. |
| 5,030,002 A | 7/1991 | North, Jr. |
| 5,040,890 A | 8/1991 | North, Jr. |
| 5,047,321 A | 9/1991 | Loken et al. |
| 5,241,180 A | 8/1993 | Ishaque et al. |
| 5,245,318 A | 9/1993 | Tohge et al. |

(Continued)

FOREIGN PATENT DOCUMENTS

KR  10-2006-0079164 A  7/2006

*Primary Examiner* — David Porta
*Assistant Examiner* — Faye Boosalis
(74) *Attorney, Agent, or Firm* — Bret E. Field; Bozicevic, Field & Francis LLP

(57) ABSTRACT

Aspects of the present disclosure include an optical detector scatter cap assembly. Optical detector scatter cap assemblies according to certain embodiments include a housing having a proximal end and a distal end, an orifice at the distal end of the housing, a scatter bar affixed to the housing and extending across the orifice and a cover bar that reversibly mates with the scatter bar. Also provided are systems that include the optical detector scatter cap assemblies, methods of using the systems, e.g., in sample processing, and kits that include component(s) of the optical detector scatter cap assemblies.

20 Claims, 7 Drawing Sheets

(56) References Cited

U.S. PATENT DOCUMENTS

| | | |
|---|---|---|
| 5,317,162 A | 5/1994 | Pinsky et al. |
| 5,394,430 A | 2/1995 | Huang |
| 5,464,581 A | 11/1995 | van den Engh |
| 5,483,469 A | 1/1996 | Van den Engh et al. |
| 5,602,039 A | 2/1997 | Van den Engh |
| 5,620,842 A | 4/1997 | Davis et al. |
| 5,627,040 A | 5/1997 | Bierre et al. |
| 5,643,796 A | 7/1997 | Van den Engh et al. |
| 5,675,155 A | 10/1997 | Pentoney, Jr. et al. |
| 5,700,692 A | 12/1997 | Sweet |
| 5,949,073 A | 9/1999 | Shimoyama |
| 6,372,506 B1 | 4/2002 | Norton |
| 6,809,804 B1 | 10/2004 | Yount et al. |
| 6,813,017 B1 | 11/2004 | Hoffman et al. |
| 6,821,740 B2 | 11/2004 | Darzynkiewicz et al. |
| 6,879,397 B2 | 4/2005 | Lloyd |
| 7,007,845 B2 | 3/2006 | Aoshima et al. |
| 7,014,326 B2 | 3/2006 | Danagher et al. |
| 7,129,505 B2 | 10/2006 | Oostman, Jr. et al. |
| 7,199,369 B1 | 4/2007 | Heverly |
| 7,201,875 B2 | 4/2007 | Norton et al. |
| 7,544,326 B2 | 6/2009 | Norton et al. |
| 8,140,300 B2 | 3/2012 | Dunne et al. |
| 8,184,285 B2 | 5/2012 | Moser et al. |
| 8,233,146 B2 | 7/2012 | Chen |
| 8,525,119 B2 | 9/2013 | Luhta et al. |
| 8,686,463 B2 | 4/2014 | Kitajima |
| 8,753,573 B2 | 6/2014 | Van Den Engh et al. |
| 8,836,935 B1 | 9/2014 | Meeks et al. |
| 8,975,595 B2 | 3/2015 | Norton et al. |
| 9,092,034 B2 | 7/2015 | Vrane et al. |
| 9,095,494 B2 | 8/2015 | Warner et al. |
| 9,097,640 B2 | 8/2015 | Goldberg et al. |
| 2007/0121095 A1 | 5/2007 | Lewis |
| 2013/0131447 A1* | 5/2013 | Benning ............ A61B 1/00137 600/109 |
| 2015/0377860 A1 | 12/2015 | Schentag et al. |

\* cited by examiner

OPTICAL DETECTOR SCATTER CAP ASSEMBLY HAVING A REMOVABLE SCATTER BAR AND METHODS OF USING THE SAME

CROSS-REFERENCE TO RELATED APPLICATIONS

Pursuant to 35 U.S.C. §119(e), this application claims priority to the filing date of U.S. Provisional Patent Application Ser. No. 62/181,092, filed Jun. 17, 2015, the disclosure of which application is incorporated herein by reference.

INTRODUCTION

Flow cytometry is a technique used to characterize and sort biological material, such as cells of a blood sample or particles of interest in any other type of biological or chemical sample. The technique may be used to record distributions or physically sort the biological material.

A flow cytometer typically includes a sample reservoir for receiving a fluid sample, such as a blood sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through a laser at an interrogation point. As components of the flow stream move through the laser, light from the compounds in the flow stream is emitted (e.g., in the form of fluorescence) and scattered. Variations in the materials, such as morphologies or fluorescent label, cause variations in the observed light which allow for characterization by collecting the light onto an optical detector.

Fluorescence from a sample in a flow stream is much dimmer than the irradiating laser beam that generated the scattered light and fluorescence signals. To minimize the contribution of the excitation laser in the detectors, various means are employed to remove this light prior to the analysis. For a jet-in-air cell sorter, the interaction of the laser with the stream produces a disk of light that needs to be blocked. As a result, the scatter or obscuration bars in a jet-in-air cell sorter are thin bars that block the disk of light scattered from the stream while allowing collection of the greatest amount of valuable fluorescent signal from the sample.

The prior art for a jet in air cell sorter has been a scatter cap, which is a hollowed out cylinder that slips over the top of a light collection device, e.g., as depicted in FIG. 1. The end of the cylinder has a lip to keep it from slipping on further than the top of the light collection device and across this lip is a bar, usually 2 mm in width. For this cap to function well, the excitation laser must be exquisitely aligned to intersect the center of the stream at the appropriate point as well as the center of the obscuration bar. Prior art solutions require an expert to align the laser well enough to use the scatter bar to detect very small cells or particles.

SUMMARY

Aspects of the present disclosure include an optical detector scatter cap assembly. Optical detector scatter cap assemblies according to certain embodiments include a housing having a proximal end and a distal end, an orifice at the distal end of the housing, a scatter bar affixed to the housing and extending across the orifice and a cover bar that reversibly mates with the scatter bar. Embodiments of the present disclosure include one or more cover bars configured to be reversibly affixed to the scatter bar on the optical detector scatter cap assembly housing allowing the user to match the scatter bar style with the application at hand. As described in greater detail below, cover bars may in certain embodiments, be a magnetic material such as an oxide-magnetic steel. In one example, the optical detector scatter cap assembly housing includes one or more magnets and alignment components to allow the user to reliably and repeatedly replace the different shaped and sized cover bars onto the optical detector scatter cap assembly housing.

Also provided are systems (e.g., a flow cytometer) having an optical detector scatter cap assembly coupled to a detector for detecting one or more wavelengths of light as well as methods for assaying a sample where a sample (e.g., in a flow stream) is irradiated with a light source and one or more of fluorescence and scattered light from the sample is detected and measured by a detector coupled to an optical detector scatter cap assembly. Kits having an optical detector scatter cap and two or more cover bars configured to be reversibly mated with the optical detector scatter cap are also described.

DETAILED DESCRIPTION

Figure 1:
FIG. 1 provides a view of a scatter cap according to the prior art.

Aspects of the present disclosure include an optical detector scatter cap assembly. Optical detector scatter cap assemblies according to certain embodiments include a housing having a proximal end and a distal end, an orifice at the distal end of the housing, a scatter bar affixed to the housing and extending across the orifice and a cover bar that reversibly mates with the scatter bar. Also provided are systems (e.g., a flow cytometer) having an optical detector scatter cap assembly coupled to a detector for detecting one or more wavelengths of light as well as methods for assaying a sample where a sample in a flow stream is irradiated with a light source and one or more of fluorescence and scattered light from the sample is detected and measured by a detector coupled to an optical detector scatter cap assembly. Kits having an optical detector scatter cap and two or more cover bars configured to be reversibly mated with the optical detector scatter cap are also described.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides an optical detector scatter cap assembly. In further describing embodiments of the disclosure, components of the subject optical detector scatter cap assembly are first described in greater detail. Next, systems and methods for measuring light from a sample (e.g., fluorescent and scattered light from a flow stream) with a detector coupled to an optical detector scatter cap assembly are described. Kits having an optical detector scatter cap assembly and two or more cover bars are also provided.

Optical Detector Scatter Cap Assembly

As summarized above, aspects of the present disclosure include an optical detector scatter cap assembly. In embodiments of the present disclosure, the subject optical detector scatter cap assembly facilitates the collection of light from an irradiated sample (e.g., in a flow stream) by a detector and reduces the amount of incident light from reaching the detector surface. By "incident" light is meant the light impinged on the sample by the irradiating light source (e.g., a laser, LED or flash lamp). In some instances, optical detector scatter cap assemblies reduce the amount of incident light from the irradiating light source that reaches the surface of the detector by 50% or more, such as by 60% or more, such as by 75% or more, such as by 80% or more, such as by 85% or more, such as by 90% or more, such as by 95% or more, such as by 97% or more, such as by 99% or more and including reducing the amount of incident light from the irradiating light source by 99.9% or more. By reducing the amount of incident light from the irradiating light source that reaches the detector surface, detector signal intensity from fluorescence and scattered light from the sample are increased as compared to detector signals from fluorescence and scattered light collected by a detector not coupled to an optical detector scatter cap assembly. In some embodiments, detector signal intensity from fluorescence and scattered light measured by a detector coupled to the subject optical detector scatter cap assembly is increased by 10% or more as compared to detector signals from fluorescence and scattered light collected by a detector not coupled to an optical detector scatter cap assembly, such as by 25% or more, such as by 50% or more, such as by 75% or more, such as by 90% or more and including by 95% or more. In certain embodiments, detector signal intensity from fluorescence and scattered light measured by a detector coupled to the subject optical detector scatter cap assembly is increased by 1.5-fold or more as compared to detector signals from fluorescence and scattered light measured by a detector not coupled to an optical detector scatter cap assembly, such as by 2-fold or more, such as by 3-fold or more, such as by 5-fold or more and including by 10-fold or more.

The subject optical detector scatter cap assembly includes a housing having a proximal end and a distal end having an orifice and a scatter bar affixed to the housing and extending across the orifice. Depending on the type and size of detector (as described in greater detail below), the length of the housing may vary ranging from 15 mm to 50 mm, such as from 20 mm to 45 mm, such as from 25 mm to 40 mm and including from 30 mm to 35 mm. The width of the housing may also vary, ranging from 5 mm to 50 mm, such as from 10 mm to 45 mm, such as from 15 mm to 40 mm, such as from 20 mm to 35 mm and including 25 mm to 30 mm. The cross-sectional shape of the housing may be any convenient shape depending on the type of detector (e.g., quadrant photodiode) and may be a rectilinear shape, e.g., squares, rectangles, trapezoids, triangles, hexagons, etc., curvilinear shapes, e.g., circles, ovals, as well as irregular shapes, e.g., a parabolic bottom portion coupled to a planar top portion. In certain embodiments, the housing has a circular cross-sectional shape and has a diameter that ranges from 5 mm to 50 mm, such as from 10 mm to 45 mm, such as from 15 mm to 40 mm, such as from 20 mm to 35 mm and including 25 mm to 30 mm.

The distal end of the housing includes an orifice for light to reach the detector. The size of the orifice may vary, having a width that ranges from 5 mm to 50 mm, such as from 10 mm to 45 mm, such as from 15 mm to 40 mm, such as from 20 mm to 35 mm and including 25 mm to 30 mm. The orifice may be any convenient shape depending on the type of detector (e.g., quadrant photodiode) and may be a rectilinear shape, e.g., squares, rectangles, trapezoids, triangles, hexagons, etc., curvilinear shapes, e.g., circles, ovals, as well as irregular shapes, e.g., a parabolic bottom portion coupled to a planar top portion. In certain embodiments, the orifice is circular and has a diameter that ranges from 5 mm to 50 mm, such as from 10 mm to 45 mm, such as from 15 mm to 40 mm, such as from 20 mm to 35 mm and including 25 mm to 30 mm. The total area of the orifice may range from 1 to 500 mm$^2$, such as from 2 to 400 mm$^2$, such as from 3 to 250 mm$^2$, such as 5 to 150 mm$^2$ and including from 10 to 100 mm$^2$.

The housing of the optical detector scatter cap assembly is configured to be immobilized onto a detector. In embodiments, the housing may include a fastener to immobilize the housing to the detector. Any convenient fastening protocol may be employed, where fasteners of interest may include but are not limited to protrusions, grooves, latches, holes or a screw thread. In some embodiments, the housing includes one or more protrusions. In other embodiments, the housing includes one or more grooves. In yet other embodiments, the housing includes a screw thread and the optical detector scatter cap assembly is screw threaded with the detector.

The housing of the optical detector scatter cap assembly may be formed from any suitable material, including, but not limited to metal, glass, ceramic, or plastic. In certain embodiments, the housing is formed from a plastic, such as a rigid plastic, polymeric or thermoplastic material. For example, suitable plastics may include polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the housing is formed from a polyester, where polyesters of interest may include, but are not limited to poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ϵ-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); Mylar™.

In certain embodiments, the housing of the optical detector scatter cap assembly is formed from a metal, such as aluminum, chromium, cobalt, copper, gold, indium, iron, lead, nickel, tin, steel (e.g., stainless steel), silver, zinc and combinations and alloys thereof. In other embodiments, the shaft is formed from a metal alloy, such as an aluminum alloy, aluminum-lithium alloy, an aluminum-nickel-copper alloy, an aluminum-copper alloy, an aluminum-magnesium alloy, an aluminum-magnesium oxide alloy, an aluminum-silicon alloy, an aluminum-magnesium-manganese-platinum alloy, a cobalt alloy, a cobalt-chromium alloy, a cobalt-tungsten alloy, a cobalt-molybdenum-carbon alloy, a cobalt-chromium-nickel-molybdenum-iron-tungsten alloy, a copper alloy, a copper-arsenic alloy, a copper-beryllium alloy, a copper-silver alloy, a copper-zinc alloy (e.g., brass), a copper-tin alloy (e.g., bronze), a copper-nickel alloy, a copper-tungsten alloy, a copper-gold-silver alloy, a copper-nickel-iron alloy, a copper-manganese-tin alloy, a copper-aluminum-zinc-tin alloy, a copper-gold alloy, a gold alloy, a gold-silver alloy, an indium alloy, an indium-tin alloy, an indium-tin oxide alloy, an iron alloy, an iron-chromium alloy (e.g., steel), an iron-chromium-nickel alloy (e.g., stainless steel), an iron-silicon alloy, an iron-chromium-molybdenum alloy, an iron-carbon alloy, an iron-boron alloy, an iron-magnesium alloy, an iron-manganese alloy, an iron molybdenum alloy, an iron-nickel alloy, an iron-phosphorus alloy, an iron-titanium alloy, an iron-vanadium alloy, a lead alloy, a lead-antimony alloy, a lead-copper alloy, a lead-tin alloy, a lead-tin-antimony alloy, a nickel alloy, a nickel-manganese-aluminum-silicon alloy, a nickel-chromium alloy, a nickel-copper alloy, a nickel, molybdenum-chromium-tungsten alloy, a nickel-copper-iron-manganese alloy, a nickel-carbon alloy, a nickel-chromium-iron alloy, a nickel-silicon alloy, a nickel-titanium alloy, a silver alloy, a silver-copper alloy (e.g., sterling silver) a silver-copper-germanium alloy (e.g., Argentium sterling silver), a silver-gold alloy, a silver-copper-gold alloy, a silver-platinum alloy, a tin alloy, a tin-copper-antimony alloy, a tin-lead-copper alloy, a tin-lead-antimony alloy, a titanium alloy, a titanium-vanadium-chromium alloy, a titanium-aluminum alloy, a titanium-aluminum-vanadium alloy, a zinc alloy, a zinc-copper alloy, a zinc-aluminum-magnesium-copper alloy, a zirconium alloy, a zirconium-tin alloy or a combination thereof. In certain embodiments, the housing of the optical detector scatter cap assembly is formed from a magnetic metal, such as an oxide-coated magnetic steel.

The housing includes a scatter bar that extends across the orifice. In some embodiments, the scatter bar is integrated into the distal end of the housing. In other embodiments, the scatter bar is irreversibly affixed to the distal end of the housing, such as for example with a permanent adhesive, welded to the housing, or co-molded with the housing. In embodiments, the scatter bar divides the orifice at the distal end of the housing into two sections. The size (in area, mm$^2$) of each orifice section may vary depending on the size of the housing and detector surface area, ranging from 0.5 to 250 mm$^2$, such as from 1 to 200 mm$^2$, such as from 1.5 to 125 mm$^2$, such as 2.5 to 75 mm$^2$ and including from 5 to 50 mm$^2$. Depending on the position of the scatter bar, each orifice section may have the same or different size. In some embodiments, the scatter bar is positioned across the orifice such that each orifice section has the same size. In other embodiments, the scatter bar is positioned across the orifice such that each orifice has a different size. Where the orifice sections have different sizes, the difference between the larger orifice section and smaller orifice section may be 5% or more, such as 10% or more, such as 15% or more, such as 25% or more, such as 50% or more and including 75% or more. For example, the larger orifice section may be 0.5 mm² or greater, such as 1 mm² or greater, such as 2 mm² or greater, such as 5 mm² or greater, such as 7.5 mm² or greater, such as 10 mm² or greater, such as 15 mm² or greater, such as 25 mm² or greater, such as 50 mm² or greater and including 100 mm² or greater.

The scatter bar may be positioned anywhere across the distal of housing depending on the alignment of the detector with the irradiating light source (as described in greater detail below). For example, in some embodiments the scatter bar is positioned to extend across the center of the orifice (i.e., dividing the orifice into equally sized orifice sections). In other embodiments, the scatter bar is positioned off-center across the orifice (i.e., dividing the orifice into unequally sized orifice sections), such as 0.1 mm or more off-center, such as 0.5 mm or more, such as 1 mm or more, such as 1.5 mm or more, such as 2 mm or more, such as 2.5 mm or more, such as 3 mm or more, such as 3.5 mm or more, such as 4 mm or more, such as 4.5 mm or more, such as 5 mm or more and including 5.5 mm or more off-cent across the orifice.

The scatter bar has a width that varies, ranging from 0.1 mm to 2 mm, such as from 0.2 mm to 1.9 mm, such as from 0.3 mm to 1.8 mm, such as from 0.4 mm to 1.7 mm, such as from 0.5 mm to 1.6 mm, such as from 0.6 mm to 1.5 mm and including 1 mm. In certain embodiments, the width of the scatter bar is 2 mm. The scatter bar may be any convenient shape, such as a rectilinear shape (e.g., squares, rectangles, trapezoids, triangles, hexagons, etc.), a curvilinear shape (e.g., circles, ovals, etc.) as well as irregular shapes, (e.g., a parabolic bottom portion coupled to a planar top portion). In certain embodiments, the scatter bar is rectangular.

In certain embodiments, the scatter bar includes one or more slits. The slit aperture may be any convenient shape, including but not limited to an oval, rectangle or other suitable polygon. In certain embodiments, the slit aperture is rectangular. The dimensions of the slit aperture may vary, having a length which ranges from 1 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 μm to 250 μm, such as from 2 μm to 225 μm, such as from 5 μm to 200 μm, such as from 10 μm to 150 μm, and including from 15 μm to 125 μm, for example a slit having an aperture width of 100 μm.

The scatter bar may be formed from the same or different material from the housing. In some embodiments, the scatter bar is formed from the same material as the housing (e.g., where the scatter bar is integrated into the housing). In other embodiments, the scattered bar is formed from a different material. In some instances, the scatter bar is formed from a metal, such as aluminum, chromium, cobalt, copper, gold, indium, iron, lead, nickel, tin, steel (e.g., stainless steel), silver, zinc and combinations and alloys thereof. In other embodiments, the shaft is formed from a metal alloy, such as an aluminum alloy, aluminum-lithium alloy, an aluminum-nickel-copper alloy, an aluminum-copper alloy, an aluminum-magnesium alloy, an aluminum-magnesium oxide alloy, an aluminum-silicon alloy, an aluminum-magnesium-manganese-platinum alloy, a cobalt alloy, a cobalt-chromium alloy, a cobalt-tungsten alloy, a cobalt-molybdenum-carbon alloy, a cobalt-chromium-nickel-molybdenum-iron-tungsten alloy, a copper alloy, a copper-arsenic alloy, a copper-beryllium alloy, a copper-silver alloy, a copper-zinc alloy (e.g., brass), a copper-tin alloy (e.g., bronze), a copper-nickel alloy, a copper-tungsten alloy, a copper-gold-silver alloy, a copper-nickel-iron alloy, a copper-manganese-tin alloy, a copper-aluminum-zinc-tin alloy, a copper-gold alloy, a gold alloy, a gold-silver alloy, an indium alloy, an indium-tin alloy, an indium-tin oxide alloy, an iron alloy, an iron-chromium alloy (e.g., steel), an iron-chromium-nickel alloy (e.g., stainless steel), an iron-silicon alloy, an iron-chromium-molybdenum alloy, an iron-carbon alloy, an iron-boron alloy, an iron-magnesium alloy, an iron-manganese alloy, an iron molybdenum alloy, an iron-nickel alloy, an iron-phosphorus alloy, an iron-titanium alloy, an iron-vanadium alloy, a lead alloy, a lead-antimony alloy, a lead-copper alloy, a lead-tin alloy, a lead-tin-antimony alloy, a nickel alloy, a nickel-manganese-aluminum-silicon alloy, a nickel-chromium alloy, a nickel-copper alloy, a nickel, molybdenum-chromium-tungsten alloy, a nickel-copper-iron-manganese alloy, a nickel-carbon alloy, a nickel-chromium-iron alloy, a nickel-silicon alloy, a nickel-titanium alloy, a silver alloy, a silver-copper alloy (e.g., sterling silver) a silver-copper-germanium alloy (e.g., Argentium sterling silver), a silver-gold alloy, a silver-copper-gold alloy, a silver-platinum alloy, a tin alloy, a tin-copper-antimony alloy, a tin-lead-copper alloy, a tin-lead-antimony alloy, a titanium alloy, a titanium-vanadium-chromium alloy, a titanium-aluminum alloy, a titanium-aluminum-vanadium alloy, a zinc alloy, a zinc-copper alloy, a zinc-aluminum-magnesium-copper alloy, a zirconium alloy, a zirconium-tin alloy or a combination thereof. In certain instances, the scatter bar is formed from a magnetic metal, such as an oxide-coated magnetic steel.

In other instances, the scatter bar is formed from a plastic, such as a rigid plastic, polymeric or thermoplastic material, including polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials. In certain embodiments, the scatter bar is formed from a polyester, where polyesters of interest may include, but are not limited to poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediylalkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p- phenylene terephthalamide); polyethylene Terephthalate (e.g., Mylar™ Polyethylene Terephthalate), etc.

As described in greater detail below, a cover bar is configured to be reversibly mated with the scatter bar. In embodiments, one or both of the scatter bar and the cover bar may include a fastener to immobilize the cover bar to the scatter bar. In some embodiments, the scatter bar includes a fastener. In other embodiments, the cover bar includes a fastener. In certain embodiments, the scatter bar and the cover bar both include a fastener. Fasteners may include, but are not limited to, latches, protrusions, grooves, non-permanent adhesives (e.g., a pressure sensitive adhesive), hook and loop fasteners or one or more magnets. In some instances, the scatter bar and the cover bar are reversibly mated with a latch. In other embodiments, the scatter bar and the cover bar are reversibly mated with a hook and loop fastener. In yet other embodiments, the scatter bar and the cover bar are reversibly mated with one or more magnets. In certain embodiments, one or both of the scatter bar and cover bar are magnetic and are reversibly mated together by a magnetic force.

The distal end of the housing may also include one or more aligners for positioning the cover bar onto the scatter bar. For example, the distal end of the housing may include 2 or more aligners, such as 3 or more aligners, such as 4 or more aligners and including 6 or more aligners. The aligners may be positioned on top of the scatter bar or adjacent to the scatter bar. In one example, the aligners are positioned adjacent to the scatter bar. In another example, the aligner is positioned on top of the scatter bar. Suitable aligners may include but are not limited to brackets, clips, latches, grooves or protrusions. In some embodiments, the aligner includes two brackets adjacent to the scatter bar. In other embodiments, the aligner includes two latches adjacent to the scatter bar. In yet other embodiments, the aligner includes one or more protrusions on the scatter bar. In still other embodiments, the aligner includes one or more grooves on the scatter bar. In still other embodiments, the aligner includes one or more notches on the scatter bar. In certain embodiments, the fastener (as described above) is configured to mate with an aligner. For example, the fastener may be one or more magnets which are configured to be positioned into a groove or notch. Placement of the magnet in the notch is sufficient, in these embodiments, to both align and fastener the cover bar to the scatter bar.

As summarized above, the subject optical detector scatter cap assembly includes a cover bar that is configured to be reversibly mated with the scatter bar. In embodiments, the cover bar has a width that is equal to or greater than the scatter bar. For example, the width of cover bars of interest may range from 2 mm to 10 mm, such as from 2.1 mm to 9.5 mm, such as from 2.2 mm to 9 mm, such as from 2.3 mm to 8.5 mm, such as from 2.4 mm to 8 mm, such as from 2.5 mm to 7.5 mm and including from 3 mm to 6 mm. The cover bar may be any convenient shape, such as a rectilinear shape (e.g., squares, rectangles, trapezoids, triangles, hexagons, etc.), a curvilinear shape (e.g., circles, ovals, etc.) as well as irregular shapes, (e.g., a parabolic bottom portion coupled to a planar top portion). In one example, the cover bar is rectangular. In another example, the cover bar is semi-circular. In another example, the cover bar has an asymmetric width where a first end has a width that is different from the width of a second end. For example, the cover bar may be an asymmetric polygon where a first end has a width that is greater than the width of the second end. In other embodiments, the cover bar is an asymmetric polygon where a first end has a width that is smaller than the width of the second end. The width at each end may range from 2 mm to 10 mm, such as from 2.5 mm to 7.5 mm and including from 3 mm to 6 mm. In certain embodiments, the cover bar is an asymmetric polygon having a first end having a width from 2 to 3 mm and a second end having a width from 4 to 5 mm. For example, the cover bar may be an asymmetric polygon having a first end having a 2 mm width and a second end having a 5 mm width.

As described in greater detail below, the cover bar has a shape and size that depends on the particles in the sample (e.g., in a flow stream) and source of light used to irradiate the sample. For example, where particles in the sample are 4 to 10 times the size of the wavelength of light used to irradiate the sample, the cover bar is polygonal or curvilinear and has a width that ranges from 1 mm to 5 mm, such as from 1.5 mm to 4 mm and including from 2 mm to 3 mm. For instance, where particles in the sample are 4 to 10 times the size of the wavelength of light used to irradiate the sample, the cover bar has a width that is 2 mm. In other embodiments, where particles in the sample are less than 4 times the size of the wavelength of light used to irradiate the sample, the cover bar is polygonal or curvilinear and has a width that ranges from 2 mm to 10 mm, such as from 2.5 mm to 9 mm, such as from 3 mm to 8 mm and including from 3.5 mm to 6 mm. For instance, where particles in the sample are less than 4 times the size of the wavelength of light used to irradiate the sample, the cover bar may have a width that is 2.5 mm, 3 mm, 3.5 mm, 4 mm, 4.5 mm, 5 mm, 5.5 mm or 6 mm.

In some embodiments, the cover bar has a shape and size that depends on properties of the irradiating source of the light, such as the laser beam profile or laser spot size. In some instances, the cover bar depends on the beam profile of the laser light. Where the beam profile is circular or oval, the cover bar may be polygonal or curvilinear having a width that is the same or greater than the largest dimension of the beam profile. For example, where the beam profile is circular, the cover bar is the same size as or greater than the diameter of the laser beam, such as 0.1 mm greater or more, such as 0.2 mm greater or more, such as 0.3 mm greater or more, such as 0.4 mm greater or more, such as 0.5 mm greater or more and including 1 mm greater or more than the diameter of the laser beam profile.

In certain embodiments, the cover bar includes one or more slits. The slit aperture may be any convenient shape, including but not limited to an oval, rectangle or other suitable polygon. In certain embodiments, the slit aperture is rectangular. The dimensions of the slit aperture may vary, having a length which ranges from 1 mm to 10 mm, such as from 1.25 mm to 9.5 mm, such as from 1.5 mm to 9 mm, such as from 2 mm to 8 mm, such as from 2.5 mm to 7 mm, such as from 3 mm to 6 mm and including from 3.5 mm to 5 mm. The width of the slit aperture may range from 1 µm to 250 µm, such as from 2 µm to 225 µm, such as from 5 µm to 200 µm, such as from 10 µm to 150 µm, and including from 15 µm to 125 µm, for example a slit having an aperture width of 100 µm.

In other instances, the width of the cover bar is the same as or greater than the width of the beam spot of the light source on the sample. For example, where the beam spot of the light source is a laser beam spot on the sample, the width of the cover bar is the same as or greater than the diameter of the laser beam spot on the sample, such as 0.1 mm greater or more, such as 0.2 mm greater or more, such as 0.3 mm greater or more, such as 0.4 mm greater or more, such as 0.5 mm greater or more and including 1 mm greater or more than the diameter of the laser beam spot on the sample.

As described above, one or more of the cover bar and the scatter bar may include a fastener for irreversibly mating the cover bar to the scatter bar. In some embodiments, the cover bar includes one or more fasteners. Fasteners on the cover bar of interest may include, but are not limited to latches, protrusions, grooves, non-permanent adhesives (e.g., a pressure sensitive adhesive), hook and loop fasteners or one or more magnets. In some instances, the cover bar includes one or more latches. In other embodiments, the cover bar includes one or more hook and loop fasteners. In yet other embodiments, the cover bar includes one or more magnets.

The cover bar may be formed from the same or different material as the scatter bar. In some embodiments, the cover bar is formed from the same material as the scatter bar. In other embodiments, the cover bar and scatter bar are formed from different materials. In some instances, the cover bar is formed from a metal, such as aluminum, chromium, cobalt, copper, gold, indium, iron, lead, nickel, tin, steel (e.g., stainless steel), silver, zinc and combinations and alloys thereof. In other embodiments, the shaft is formed from a metal alloy, such as an aluminum alloy, aluminum-lithium alloy, an aluminum-nickel-copper alloy, an aluminum-copper alloy, an aluminum-magnesium alloy, an aluminum-magnesium oxide alloy, an aluminum-silicon alloy, an aluminum-magnesium-manganese-platinum alloy, a cobalt alloy, a cobalt-chromium alloy, a cobalt-tungsten alloy, a cobalt-molybdenum-carbon alloy, a cobalt-chromium-nickel-molybdenum-iron-tungsten alloy, a copper alloy, a copper-arsenic alloy, a copper-beryllium alloy, a copper-silver alloy, a copper-zinc alloy (e.g., brass), a copper-tin alloy (e.g., bronze), a copper-nickel alloy, a copper-tungsten alloy, a copper-gold-silver alloy, a copper-nickel-iron alloy, a copper-manganese-tin alloy, a copper-aluminum-zinc-tin alloy, a copper-gold alloy, a gold alloy, a gold-silver alloy, an indium alloy, an indium-tin alloy, an indium-tin oxide alloy, an iron alloy, an iron-chromium alloy (e.g., steel), an iron-chromium-nickel alloy (e.g., stainless steel), an iron-silicon alloy, an iron-chromium-molybdenum alloy, an iron-carbon alloy, an iron-boron alloy, an iron-magnesium alloy, an iron-manganese alloy, an iron molybdenum alloy, an iron-nickel alloy, an iron-phosphorus alloy, an iron-titanium alloy, an iron-vanadium alloy, a lead alloy, a lead-antimony alloy, a lead-copper alloy, a lead-tin alloy, a lead-tin-antimony alloy, a nickel alloy, a nickel-manganese-aluminum-silicon alloy, a nickel-chromium alloy, a nickel-copper alloy, a nickel, molybdenum-chromium-tungsten alloy, a nickel-copper-iron-manganese alloy, a nickel-carbon alloy, a nickel-chromium-iron alloy, a nickel-silicon alloy, a nickel-titanium alloy, a silver alloy, a silver-copper alloy (e.g., sterling silver) a silver-copper-germanium alloy (e.g., Argentium sterling silver), a silver-gold alloy, a silver-copper-gold alloy, a silver-platinum alloy, a tin alloy, a tin-copper-antimony alloy, a tin-lead-copper alloy, a tin-lead-antimony alloy, a titanium alloy, a titanium-vanadium-chromium alloy, a titanium-aluminum alloy, a titanium-aluminum-vanadium alloy, a zinc alloy, a zinc-copper alloy, a zinc-aluminum-magnesium-copper alloy, a zirconium alloy, a zirconium-tin alloy or a combination thereof. In certain instances, the cover bar is formed from a magnetic metal, such as an oxide-coated magnetic steel.

Optical detector scatter caps of the invention may have spots for very small magnets as well as alignment features. Cover bars that mate with these optical detector scatter caps are employed in the final optical detector scatter cap assemblies. Where desired, the optical detector scatter caps and/or cover bars may be fabricated from oxide-coated magnetic steel as discussed above. These features allow for easy and consistent placement of various cover bar styles and the black oxide coating minimizes reflection from the surface of the cover bar.

For the detection of the scatter from a particle that is bigger than the laser wavelength, scatter in the forward direction is peaked in the direction of the laser. For a particle much smaller than the laser wavelength, the scatter is no longer peaked, and is very much diminished. In the case of the small particle, it is desirable to block as much of the incident laser as possible in order to see the small particles dim scatter signature. Because the scatter is not peaked in the forward direction, it is possible to use a thick scatter bar, removing the unwanted light while letting enough of the scattered light through to detect the particle.

Figure 2:
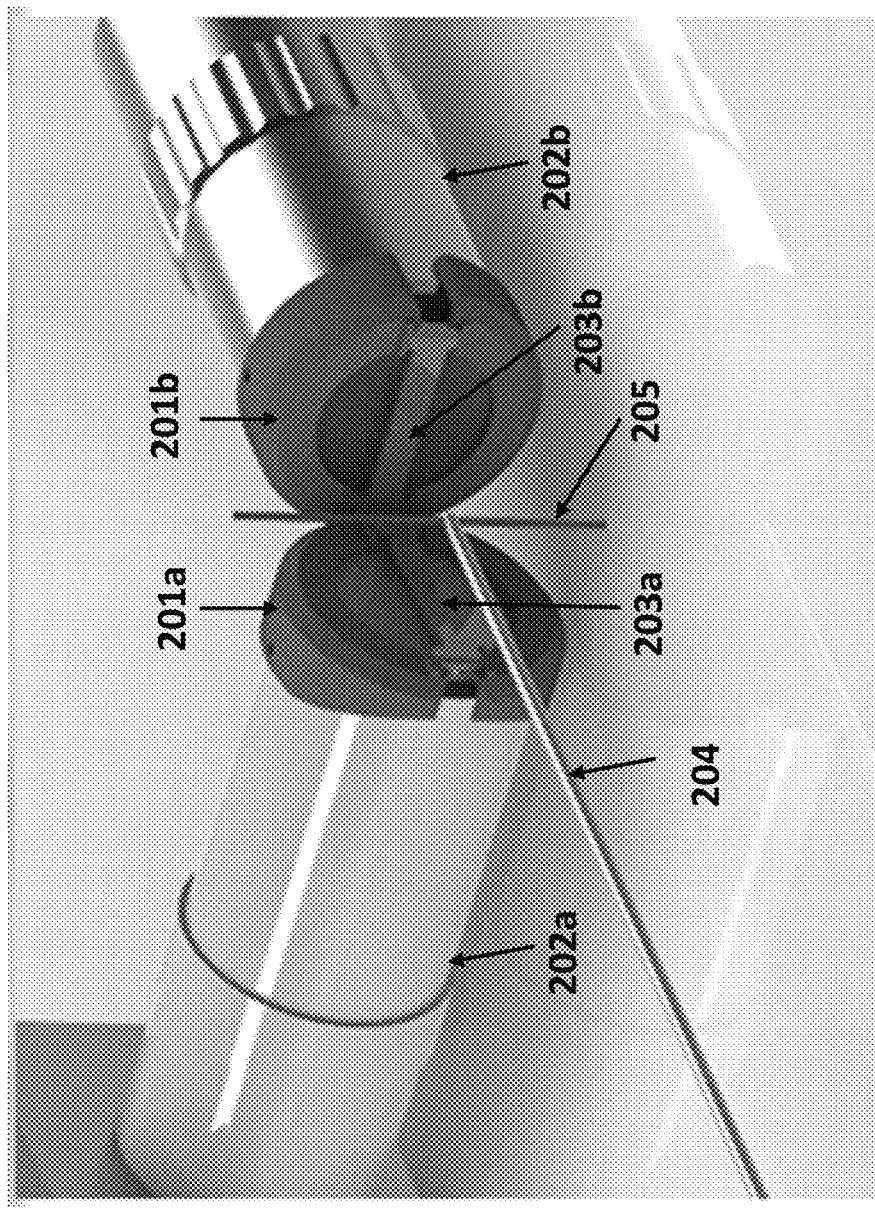
FIG. 2 provides a view of a two optical detector scatter cap assemblies coupled to detectors according to certain embodiments.

Examples of optical detector scatter cap assemblies having removable cover bars are depicted in FIGS. 2 to 6. FIG. 2 depicts two different optical detector scatter cap assemblies (201a and 201b) coupled to two detectors (202a and 202b). As shown in FIG. 2, the reversibly mated cover bars (203a and 203b) align with incident irradiating light 204 impinged on flow stream 205, thereby reducing the amount of incident light from the irradiating light source that reaches the detector surface.

Figure 3:
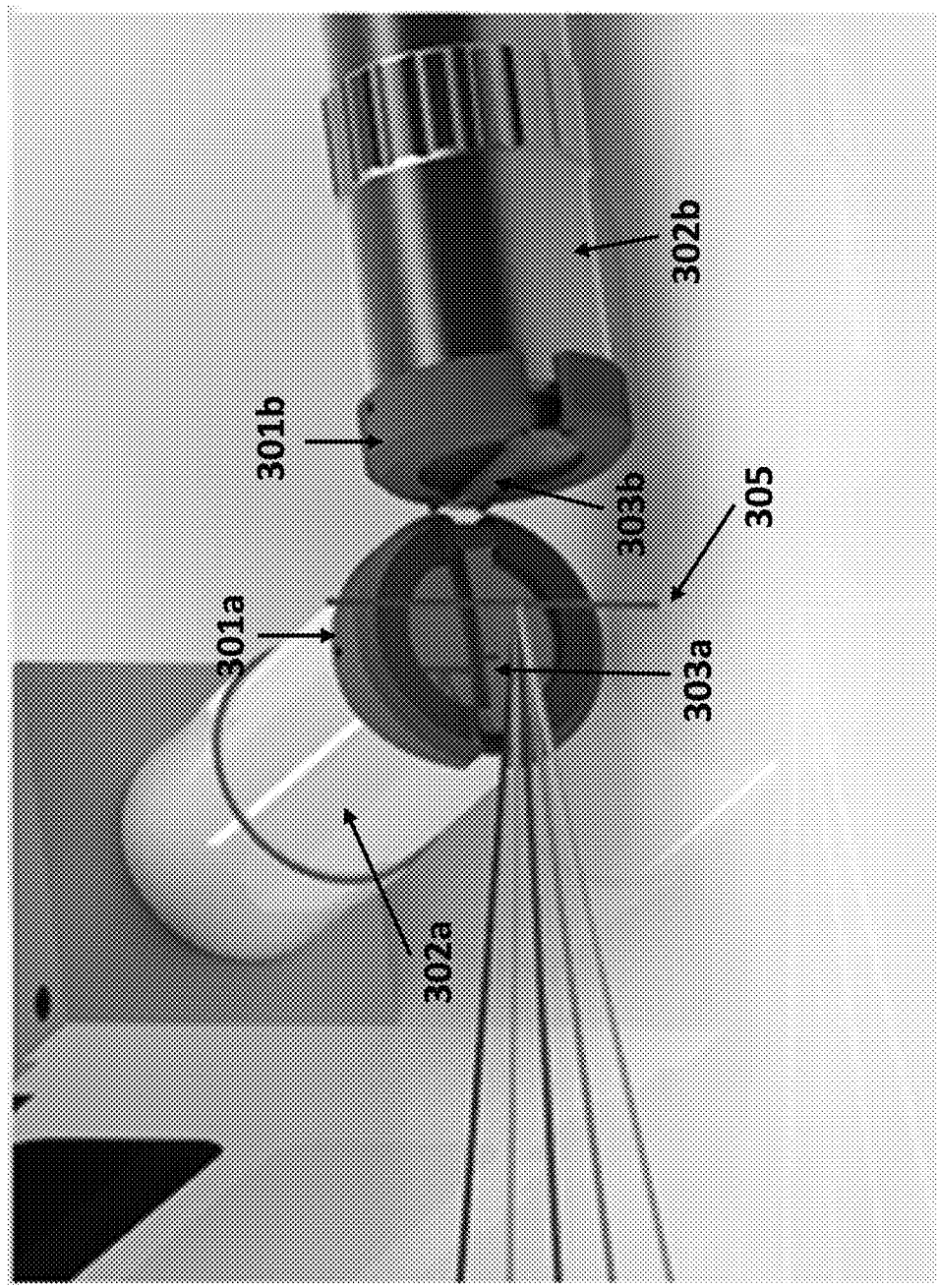
FIG. 3 provides a view of a two optical detector scatter cap assemblies coupled to detectors according to certain embodiments.

FIG. 3 depicts two different optical detector cap assemblies (301a and 301b) coupled to two detectors (302a and 302b). In FIG. 3, 302a is configured to detect the scattered and fluorescent light emanating from the stream (305), whereas 302b is configured to measure scattered light on the forward direction. In other embodiments, either detector may be configured to detect scattered light only, a combination of scattered and fluorescent light, or fluorescent light only. The scattered and fluorescent light are the result of the interaction of the cells or particles carried in the stream with a single laser, or with a plurality of lasers. In the embodiment depicted, there are 5 lasers of different wavelengths (yellow-green, blue, violet, UV, and red.)

Figure 4A:
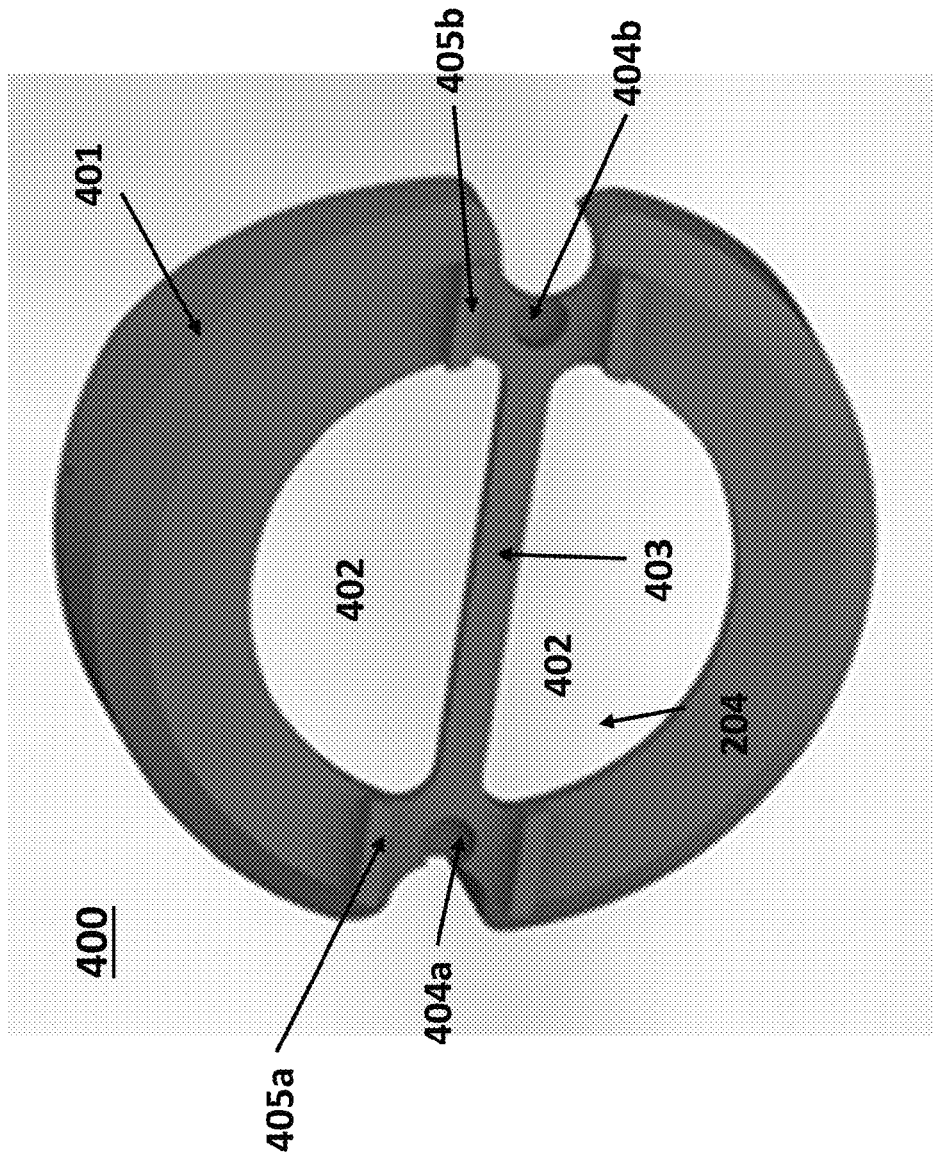
FIG. 4A provides a view of an optical detector scatter cap without a cover bar according to certain embodiments.
Figure 4B:
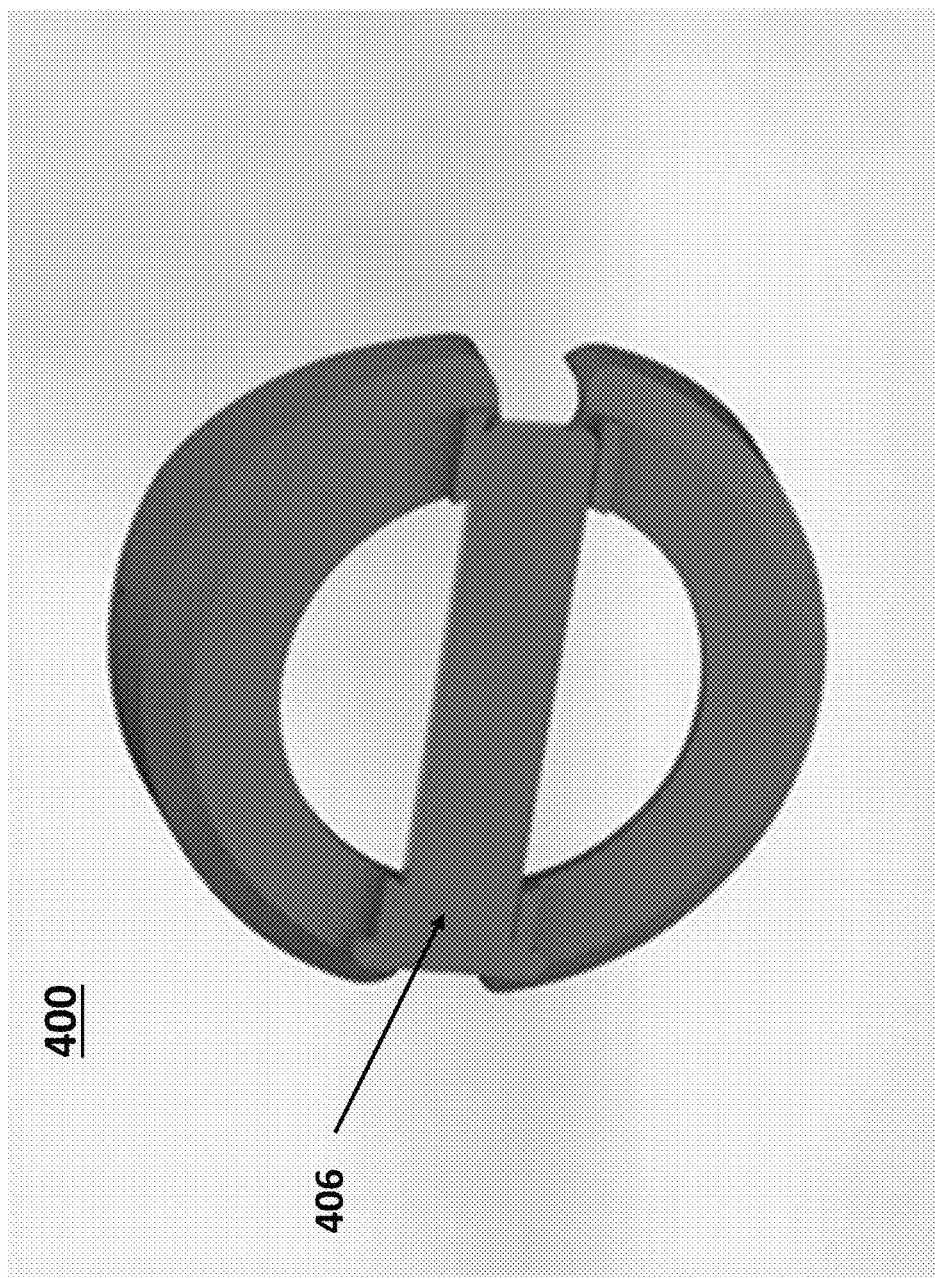
FIG. 4B provides a view of the optical detector scatter cap of FIG. 4A with a removable cover bar mated therewith.

FIGS. 4A-4B depict an optical detector scatter cap assembly according to certain embodiments. FIG. 4A depicts the optical detector scatter cap 400 without mated cover bar. Optical detector scatter cap 400 includes a housing 401 having a proximal end and distal end, the distal end having orifice 402. Scatter bar 403 is affixed to the housing and extends across orifice 402. As can be seen in the figures, optical detector scatter cap 400 has spots 404a and 404b for very small magnets that reversibly mate a cover bar with the optical detector scatter cap housing. FIG. 4A also depicts aligners 405a and 405b which are configured to align the cover bar with scatter bar 403. These features allow for easy and consistent placement of various cover bar styles or configurations.

FIG. 4B depicts optical detector scatter cap 400 mated with cover bar 406. Cover bar 406 is aligned by aligners 405a and 405b and fastened to optical detector scatter cap 400 by small magnets (not shown). The cover bars shown in FIGS. 4A-4B used oxide-coated magnetic steel which minimizes reflection from the surface of the cover bar. The black oxide coating minimizes reflection from the surface of the scatter bar.

Figure 5:
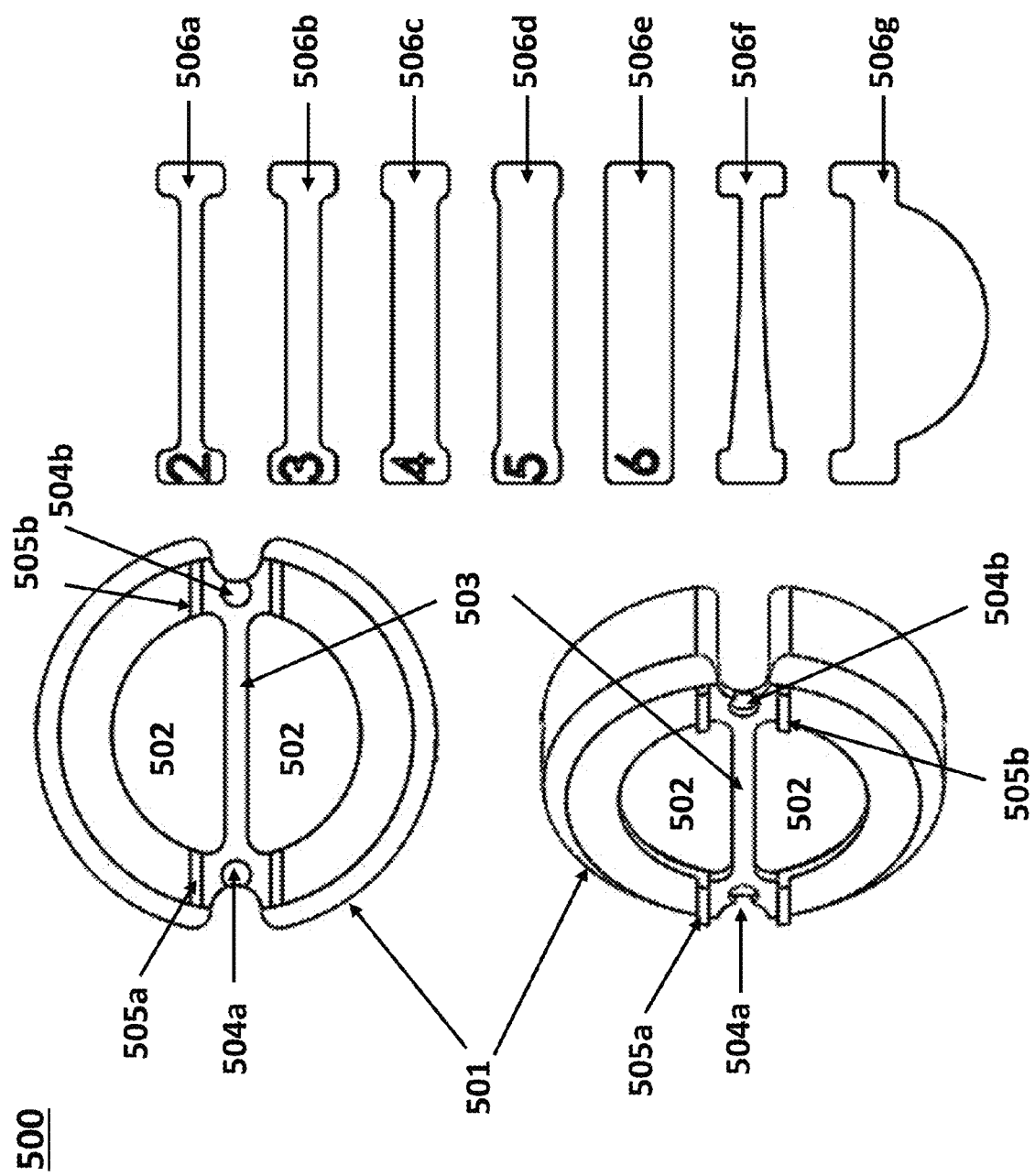
FIG. 5 depicts an illustration of a top view and side view of an optical detector scatter cap according to certain embodiments.

FIG. 5 depicts an illustration of a top view and side view of an optical detector scatter cap according to certain embodiments. Optical detector scatter cap 500 includes a housing 501 with a distal end having orifice 502. Scatter bar 503 is affixed to the housing and extends across orifice 502. The distal end of housing 501 includes holes 504a and 504b configured for positioning magnetic fasteners for mating with cover bars 506a-506g. Optical detector scatter cap 500 also includes aligners 505a and 505b for positioning the cover plate with scatter bar 503. FIG. 5 also depicts cover bars 506a-506g which differ in shape or size and allows for adjusting the amount of light that reaches the surface of the coupled detector. Cover bars 506a, 506b, 506c, 506d and 506e are examples of rectangular cover bars with different widths. Cover bar 506f is an example of an asymmetric polygonal cover bar where a first end has a first width and a second end has a second width, where the first width is greater than the second width. Cover bar 506g is an example of a curvilinear, semi-circular cover bar.

Figure 6:
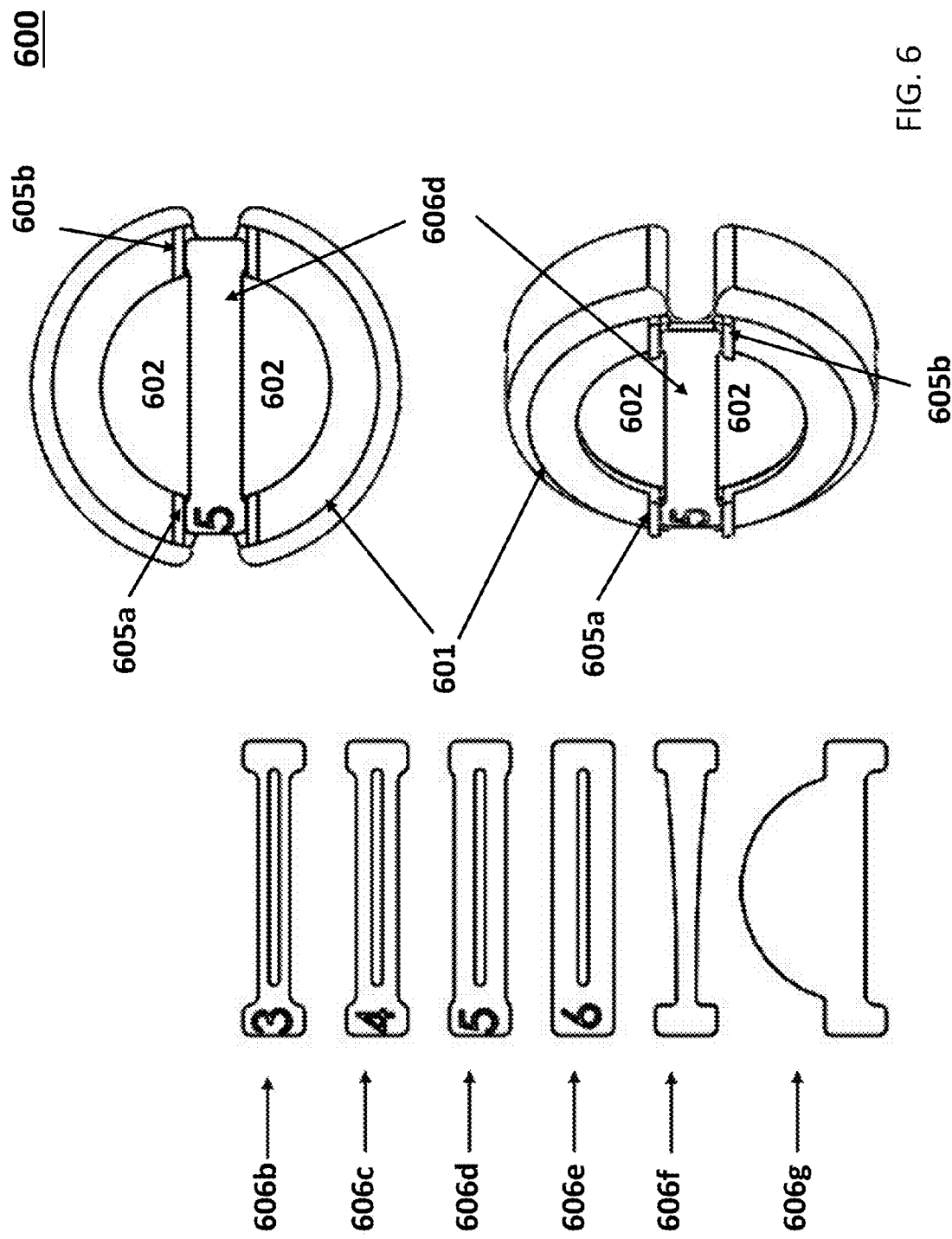
FIG. 6 depicts an illustration of a top view and side view of an optical detector scatter cap assembly according to certain embodiments.

FIG. 6 depicts an illustration of a top view and side view of an optical detector scatter cap assembly according to certain embodiments. Optical detector scatter cap 600 having housing 601 is mated with cover bar 606d using aligners 605a and 605b. As described above, cover bar 606d can be removed from optical detector scatter cap 600 and replaced with any one of cover bars 606b, 606c, 606d, 606f and 606g. Cover bars 606b, 606c, 606d and 606e are examples of rectangular cover bars having different widths. Cover bar 606f is another example of an asymmetric polygonal cover bar where a first end has a first width and a second end has a second width, where the first width is greater than the second width. Cover bar 606g is another example of a curvilinear, semi-circular cover bar.

In some instances, the optical detector scatter cap assembly is configured to couple a detector to one or more optical adjustment components. By "optical adjustment" is meant that light propagated from the sample is changed as desired before being conveyed to the detector for measurement. For example, the optical adjustment may be to focus the collected light or to separate or block specific wavelengths of light. Optical adjustment components may be any convenient device or structure which provides the desired change in the collected light and may include, but is not limited to, lenses, filters, mirrors, pinholes, slits, gratings, light refractors, and any combinations thereof. In some embodiments, the optical adjustment component is a focusing lens. In other embodiments, the optical adjustment component is a wavelength separator. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. Wavelength separation protocols of interest which may be a part of or combined with the subject flow cell nozzles, include but are not limited to, colored glass, bandpass filters, interference filters, combinations thereof, among other wavelength separating protocols.

The optical adjustment component may be configured for positioning at the distal end of the housing or a distance that is 0.01 mm or more from the distal end of the housing, such as 0.05 mm or more, such as 0.1 mm or more, such as 0.25 mm or more, such as 0.5 mm or more, such as 0.75 mm or more, such as 1 mm or more, such as 2 mm or more, such as 3 mm or more and including 4 mm or more from the distal end of the housing.

Systems for Measuring Light from a Sample

Aspects of the present disclosure include systems for measuring light emitted by a sample in a flow stream. In embodiments of the present disclosure, the subject systems are configured to measure one or more of fluorescence and scattered light from a sample (e.g., in a flow stream) while reducing the amount of incident light from the irradiating light source that reaches the surface of the detector. As summarized above, systems include a detector and an optical detector scatter cap assembly.

The subject optical detector scatter cap assembly is configured to be coupled to the detecting surface end of the detector. In embodiments, one or both of the optical detector scatter cap assembly and the detector may include a fastener to immobilize the optical detector scatter cap assembly to the detector. In some embodiments, the optical detector scatter cap assembly includes a fastener. In other embodiments, the detector includes a fastener. In certain embodiments, both the optical detector scatter cap assembly and the detector include a fastener. Any convenient fastening protocol may be employed, where fasteners of interest may include but are not limited to protrusions, grooves, latches, holes or a screw thread. In some embodiments, one or more of the optical detector scatter cap assembly and the detector include a protrusion. In other embodiments, one or more of the optical detector scatter cap assembly and the detector include a groove. In yet other embodiments, the optical detector scatter cap assembly includes a screw thread and the optical detector scatter cap assembly is screw threaded with the detector.

Systems of interest may include one or more detectors coupled to an optical detector scatter cap assembly as described herein. For example, systems may include 2 or more detectors, such as 3 or more detectors and including 5 or more detectors, each coupled to an optical detector scatter cap assembly. Where the system includes two or more detectors, the cover bar of each optical detector scatter cap assembly may be the same or different. In some embodiments, each detector is coupled to an optical detector scatter cap assembly having the same cover bar. In other embodiments, each detector is coupled to an optical detector scatter cap assembly having a different cover bar. In some embodiments, systems include a first detector coupled to a first optical detector scatter cap assembly and a second detector coupled to a second optical detector scatter cap assembly. In some instances, the first optical detector scatter cap assembly includes a rectangular cover bar and the second optical detector scatter cap assembly includes a curvilinear cover bar. In other instances, the first optical detector scatter cap assembly includes a rectangular cover bar and the second optical detector scatter cap assembly includes an asymmetric polygonal cover bar. In some embodiments, the first detector is a fluorescence detector and the second detector is a scatter detector. In other embodiments, the first detector is a forward scatter detector and the second detector is a side scatter detector. In yet other embodiments, the first detector is a side scatter detector and the second detector is a forward scatter detector.

In one example, systems of interest include a side-scatter detector coupled to an optical scatter cap assembly having an asymmetric polygonal cover bar and a forward scatter detector coupled to an optical detector scatter cap assembly having a rectangular cover bar. In another example, systems include a side-scatter detector coupled to an optical detector scatter cap assembly having a rectangular cover bar and a forward scatter detector coupled to an optical detector scatter cap assembly having an asymmetric polygonal cover bar. In yet another example, systems include a side-scatter detector coupled to an optical detector scatter cap assembly having a rectangular cover bar and a forward scatter detector coupled to an optical detector scatter cap assembly having a curvilinear (e.g., semi-circle) cover bar. In yet another example, systems include a side-scatter detector coupled to an optical detector scatter cap assembly having a curvilinear (e.g., semi-circle) cover bar and a forward scatter detector coupled to an optical detector scatter cap assembly having an asymmetric polygonal cover bar. In still another example, systems include a side-scatter detector coupled to an optical detector scatter cap assembly having a curvilinear (e.g., semi-circle) cover bar and a forward scatter detector coupled to an optical detector scatter cap assembly having a rectangular cover bar.

Detectors of interest may include, but are not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the fluorescent or scattered light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

The number of photodetectors in the subject systems may vary, as desired, such as 1 or more, such as 2 or more, such as 3 or more, such as 5 or more and including 10 or more photodetectors. Where the subject systems include more than one photodetector, each photodetector may be the same, or the collection of two or more photodetectors may be a combination of different photodetectors.

In certain embodiments, the detector is a positional sensing protocol, including but not limited to position sensing photosensors, photodetectors, active pixel sensors (APS) and quadrant photodiodes. In certain embodiments, the detector is a quadrant photodiode. Where the detector is a quadrant photodiode, the active detecting surface area of each region of the quadrant photodiode may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$. In some instances, the detector is a photodiode array having more than one photodiode, such as two or more photodiodes, such as three or more, such as five or more and including 10 or more photodiodes.

The detector may be positioned at a distance from the sample depending on the type of irradiating light source and characteristics of the sample (e.g., particle sizes in the sample). For example, the detector may be positioned 0.01 mm or more from the sample, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 or more from the sample. The detector may also be positioned at an angle with respect to the sample which varies. For example, the detector may be positioned at an angle with respect to the sample which ranges from 10° to 90°, such as from 15° to 85°, such as from 20° to 80°, such as from 25° to 75° and including from 30° to 60°. In certain embodiments, the detector is positioned at a 90° angle with respect to the sample. In some embodiments, systems include a detector that is positioned to detect forward scattered light from the sample. In other embodiments, systems include a detector that is positioned to detect side scattered light from the sample. In yet other embodiments, systems include a detector that is positioned to detect fluorescence from the sample.

In some embodiments, systems of interest include one or more light sources for irradiating a sample. The light source may be a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

In certain embodiments, the light source is a laser. In some instances, the subject systems include a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the subject systems include a dye laser, such as a stilbene, coumarin or rhodamine laser. In yet other instances, lasers of interest include a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, the subject systems include a solid-state laser, such as a ruby laser, an Nd:YAG laser, NdCrYAG laser, Er:YAG laser, Nd:YLF laser, Nd:YVO$_4$ laser, Nd:YCa$_4$O(BO$_3$)$_3$ laser, Nd:YCOB laser, titanium sapphire laser, thulim YAG laser, ytterbium YAG laser, ytterbium$_2$O$_3$ laser or cerium doped lasers and combinations thereof.

The subject systems may include one or more light sources, as desired, such as two or more light sources, such as three or more light sources, such as four or more light sources, such as five or more light sources and including ten or more light sources. The light source may include any combination of types of light sources. For example, in some embodiments, the subject systems include an array of lasers, such as an array having one or more gas lasers, one or more dye lasers and one or more solid-state lasers. In other instances, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., near-IR LED or laser). In yet other instances, the light source is a plurality of narrow band light sources each emitting specific wavelengths, such as two or more lasers, such as three or more lasers including 5 or more lasers. In still other instances, the light source is an array of two or more LEDs, such as an array of three or more LEDs, such as an array of five or more LEDs, including an array of ten or more LEDs.

In some embodiments, light sources emit light having wavelengths ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a plurality of narrow band light sources emitting wavelengths ranging from 200 nm to 900 nm. For example, the light source may be plurality of narrow band LEDs (1 nm-25 nm) each independently emitting light having a range of wavelengths between 200 nm to 900 nm. In some embodiments, the narrow band light source is one or more narrow band lamps emitting light in the range of 200 nm to 900 nm, such as a narrow band cadmium lamp, cesium lamp, helium lamp, mercury lamp, mercury-cadmium lamp, potassium lamp, sodium lamp, neon lamp, zinc lamp or any combination thereof. In other embodiments, the narrow band light source includes one or more lasers emitting light in the range of 200 nm to 1000 nm, such as gas lasers, excimer lasers, dye lasers, metal vapor lasers and solid-state laser as described above.

Depending on the assay protocol, the subject systems may be configured to irradiate the sample in continuous or in discrete intervals. For example, in some embodiments, systems may be configured to irradiate the sample continuously. Where the light includes two or more light sources, the sample may be continuously irradiated by all of the light sources simultaneously. In other instances, the sample is continuously irradiated with each light source sequentially. In other embodiments, the sample may be irradiated in regular intervals, such as irradiated the sample every 0.001 microseconds, every 0.01 microseconds, every 0.1 microseconds, every 1 microsecond, every 10 microseconds, every 100 microseconds and including every 1000 microseconds.

The light source may be positioned at a distance from the sample which varies depending on the type of light source and characteristics of the sample (e.g., flow stream width, particle sizes of interest). For example, the light source may be positioned 0.01 mm or more from the sample, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the sample. The light source may also be positioned at an angle with respect to the sample which also varies. For example, the light source may be positioned at an angle with respect to the sample which ranges from 10° to 90°, such as from 15° to 85°, such as from 20° to 80°, such as from 25° to 75° and including from 30° to 60°. In certain embodiments, the light source is positioned at a 90° angle with respect to the sample.

Each detector may also include a one or more optical adjustment components. In some instances, optical adjustment is focusing the collected light from the sample (e.g., scattered light, fluorescence) onto the detector surface or blocking or separating wavelengths of light. Optical adjustment components may be any convenient device or structure which provides the desired change in the collected light beam and may include but is not limited to lenses, mirrors, pinholes, slits, gratings, light refractors, and any combinations thereof. The detector may include one or more optical adjustment components as needed, such as two or more, such as three or more, such as four or more and including five or more optical adjustment components. In certain embodiments, the detector includes a focusing lens. In other embodiments, the detector includes one or more bandpass filters.

In some embodiments, the detector and the optical adjustment component are in optical communication, but are not physically in contact. Depending on the size of the detector, the optical adjustment component may be positioned 0.05 mm or more from the detector, 0.1 mm or more, such as 0.5 mm or more, such as 1 mm or more, such as 10 mm or more, such as 25 mm or more, such as 50 mm or more, such as 100 mm or more, such as 250 mm, or more, including 500 mm or more. In other embodiments, the optical adjustment component is physically coupled to the detector, such as with an adhesive, co-molded together or integrated together in a housing having the optical adjustment component positioned adjacent to the detector. As such, the optical adjustment component and detector may be integrated into a single unit.

In certain embodiments, the subject systems are flow cytometric systems employing the above described optical detector scatter cap assemblies for reducing the amount of incident light from an irradiating light source from a sample in a flow stream. The subject optical detector scatter cap assemblies having removable cover bars of the invention may be used with a variety of different flow cytometer systems. Suitable flow cytometry systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry,* 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. J Pathol, 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSRFortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Methods for Measuring Light from a Sample

Aspects of the disclosure also include methods for measuring light emitted from a sample (e.g., in a flow stream in a flow cytometer), where the measured light is light which has passed through an optical scatter cap assembly of the invention to a detector. Methods include, in certain embodiments, irradiating the sample with a light source, detecting light from the sample with a detector coupled to an optical scatter cap assembly and measuring the detected light at one or more wavelengths. In some embodiments, the detected light is fluorescence from the sample. In other embodiments, the detected light is scattered light from the sample, such as side-scatted light or forward-scattered light.

In some embodiments, the sample is a biological sample. The term "biological sample" is used in its conventional sense to refer to a whole organism, plant, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to a homogenate, lysate or extract prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing methods according to certain embodiments, a sample (e.g., in a flow stream of a flow cytometer) is irradiated with light from a light source. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Where methods include irradiating with a broadband light source, broadband light source protocols of interest may include, but are not limited to, a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof.

In certain embodiments, methods include irradiating the sample with one or more lasers. As discussed above, the type and number of lasers will vary depending on the sample as well as desired light collected and may be a gas laser, such as a helium-neon laser, argon laser, krypton laser, xenon laser, nitrogen laser, $CO_2$ laser, CO laser, argon-fluorine (ArF) excimer laser, krypton-fluorine (KrF) excimer laser, xenon chlorine (XeCl) excimer laser or xenon-fluorine (XeF) excimer laser or a combination thereof. In others instances, the methods include irradiating the flow stream with a dye laser, such as a stilbene, coumarin or rhodamine laser. In yet other instances, methods include irradiating the flow stream with a metal-vapor laser, such as a helium-cadmium (HeCd) laser, helium-mercury (HeHg) laser, helium-selenium (HeSe) laser, helium-silver (HeAg) laser, strontium laser, neon-copper (NeCu) laser, copper laser or gold laser and combinations thereof. In still other instances, methods include irradiating the flow stream with a solid-state laser, such as a ruby laser, an Nd:YAG laser, NdCrYAG laser, Er:YAG laser, Nd:YLF laser, $Nd:YVO_4$ laser, $Nd:YCa_4O(BO_3)_3$ laser, Nd:YCOB laser, titanium sapphire laser, thulim YAG laser, ytterbium YAG laser, $ytterbium_2O_3$ laser or cerium doped lasers and combinations thereof.

The sample may be irradiated with one or more of the above mentioned light sources, such as two or more light sources, such as three or more light sources, such as four or more light sources, such as five or more light sources and including ten or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal vapor lasers and solid-state laser as described above.

Where more than one light source is employed, the sample may be irradiated with the light sources simultaneously or sequentially, or a combination thereof. For example, the sample may be simultaneously irradiated with both light sources. In other embodiments, the flow stream is sequentially irradiated with both light sources. Where two light sources irradiate sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g. laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The time period between irradiation by each light source may also vary, as desired, being separated independently by a delay of 0.001 microseconds or more, such as 0.01 microseconds or more, such as 0.1 microseconds or more, such as 1 microsecond or more, such as 5 microseconds or more, such as by 10 microseconds or more, such as by 15 microseconds or more, such as by 30 microseconds or more and including by 60 microseconds or more. For example, the time period between irradiation by each light source may range from 0.001 microseconds to 60 microseconds, such as from 0.01 microseconds to 50 microseconds, such as from 0.1 microseconds to 35 microseconds, such as from 1 microsecond to 25 microseconds and including from 5 microseconds to 10 microseconds. In certain embodiments, the time period between irradiation by each light source is 10 microseconds. In embodiments where sample is sequentially irradiated by more than two (i.e., three or more) light sources, the delay between irradiation by each light source may be the same or different.

The sample may be irradiated continuously or in discrete intervals. In some instances, methods include irradiating the sample in the sample with the light source continuously. In other instances, the sample in is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

As discussed above, in embodiments light from the sample (e.g., fluorescence, forward-scattered light, side-scattered light, etc.) is passed through an optical detector scatter cap assembly as described herein and measured by one or more detectors. In practicing the subject methods, the light is measured at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

In using the scatter caps of the invention, where the detection of the scatter from a particle that is bigger than the laser wavelength, scatter in the forward direction is peaked in the direction of the laser. For a particle much smaller than the laser wavelength, the scatter is no longer peaked, and is very much diminished. In the case of the small particle, it is desirable to block as much of the incident laser as possible in order to see the small particle's dim scatter signature. Because the scatter is not peaked in the forward direction, it is possible to use a thick scatter bar, removing the unwanted light while letting enough of the scattered light through to detect the particle.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such 2 or more times, such as 3 or more times, such as 5 or more times and including 10 or more times. In certain embodiments, the light is measured two or more times, with the data in certain instances being averaged.

Light measurements may be taken with any convenient protocol as described above, including but not limited to optical sensors or photodetectors, such as active-pixel sensors (APSs), avalanche photodiode, quadrant photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the light from the sample (e.g., fluorescence, forward-scattered light, side-scattered light, etc.) is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the transmitted light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

In some embodiments, methods include adjusting the light before measurement with the detector. For example, the collected light may be passed through one or more additional lenses, mirrors, pinholes, slits, gratings, light refractors, and any combinations thereof. In some instances, the collected light is passed through one or more focusing lenses, such as to reduce the profile of the light directed onto the active surface of the detector. In other instances, the light from the sample is passed through one or more de-magnifying lenses, such as to increase the profile of the light directed onto the active surface of the detector.

In yet other instances, methods include further collimating the light. For example, light propagated through the subject optically aligned light collection systems may be further collimated by passing the light through one or more collimating lenses or with collimating mirrors or a combination thereof. In still other instances, methods further include passing light propagated through the subject optically aligned light collection systems through one or more wavelength separators. Wavelength separation, according to certain embodiments, may include selectively passing or blocking specific wavelengths or wavelength ranges of the polychromatic light. To separate wavelengths of light, the light may be passed through any convenient wavelength separating protocol, including but not limited to colored glass, bandpass filters, interference filters, dichroic mirrors, diffraction gratings, monochromators and combinations thereof, among other wavelength separating protocols.

In certain embodiments, the detected light (e.g., fluorescence, forward-scattered light, side-scattered light, etc.) may be further passed through fiber optics. As discussed above, suitable fiber optics protocols propagating light to the active surface of the detector include, but is not limited to, flow cytometer fiber optics protocols such as those described in U.S. Pat. No. 6,809,804, the disclosure of which is herein incorporated by reference.

In some embodiments, methods include affixing a cover bar to the distal end of the optical detector scatter cap assembly based on characteristics of the sample, such as the size of particles (e.g., cells) in the sample or the magnitude of fluorescence by particles in the sample. In some instances, the size of the affixed cover bar depends on the size of the particles in the sample. In other instances, the shape of the cover bar depends on the size of the particles in the sample.

In some embodiments, where particles in the sample are 4 to 10 times the size of the wavelength of light used to irradiate the sample, methods include affixing a cover bar that has a width that ranges from 1 mm to 5 mm, such as from 1.5 mm to 4 mm and including from 2 mm to 3 mm. In these embodiments, the cover bar may be rectangular, curvilinear or asymmetric polygonal. For example, where particles in the sample are 4 to 10 times the size of the wavelength of light used to irradiate the sample, methods may include affixing to the optical detector scatter cap assembly a rectangular cover bar that has a 2 mm width.

In other embodiments, where particles in the sample are less than 4 times the size of the wavelength of light used to irradiate the sample, methods may include affixing to the optical detector scatter cap assembly a cover bar that has a width that ranges from 2 mm to 10 mm, such as from 2.5 mm to 9 mm, such as from 3 mm to 8 mm and including from 2.5 mm to 6 mm, such as a width that is 2.5 mm, 3 mm, 3.5 mm, 4 mm, 4.5 mm, 5 mm, 5.5 mm or 6 mm. In these embodiments, the cover bar may be rectangular, curvilinear or asymmetric polygonal. For example, where particles in the sample are less than 4 times the size of the wavelength of light used to irradiate the sample, methods may include affixing to the optical detector scatter cap assembly a rectangular cover bar that has a width ranging from 2 mm-6 mm.

In some embodiments, methods include: 1) affixing a first cover bar to the distal end of an optical detector scatter cap assembly; 2) detecting and measuring light (e.g., fluorescence, forward-scattered light, side-scattered light, etc.) from a sample; 3) removing the first cover bar; and 4) affixing a second cover bar to the distal end of the optical detector scatter cap assembly. In these embodiments, the first cover bar and second cover bar may vary, as described above. In some instances, the first cover bar and the second cover bar have the same shape, but are different sizes (e.g., width). In other instances, the first cover bar and the second cover bar are the same size but have different shapes. In yet other instances, the first cover bar and the second cover bar differ in both shape and size.

In one example, methods include: 1) affixing a first rectangular cover bar to the distal end of an optical detector scatter cap assembly; 2) detecting and measuring light (e.g., fluorescence, forward-scattered light, side-scattered light, etc.) from the sample; 3) removing the first rectangular cover bar; and 4) affixing a second rectangular cover bar having a different width to the distal end of the optical detector scatter cap assembly.

In another example, methods include: 1) affixing a rectangular cover bar to the distal end of an optical detector scatter cap assembly; 2) detecting and measuring light (e.g., fluorescence, forward-scattered light, side-scattered light, etc.) from the sample; 3) removing the rectangular cover bar; and 4) affixing a curvilinear cover bar to the distal end of the optical detector scatter cap assembly.

In another example, methods include: 1) affixing a curvilinear cover bar to the distal end of an optical detector scatter cap assembly; 2) detecting and measuring light (e.g., fluorescence, forward-scattered light, side-scattered light, etc.) from the sample; 3) removing the curvilinear cover bar; and 4) affixing a rectangular cover bar to the distal end of the optical detector scatter cap assembly.

In another example, methods include: 1) affixing a rectangular cover bar to the distal end of an optical detector scatter cap assembly; 2) detecting and measuring light (e.g., fluorescence, forward-scattered light, side-scattered light, etc.) from the sample; 3) removing the rectangular cover bar;

and 4) affixing an asymmetric polygonal cover bar to the distal end of the optical detector scatter cap assembly.

In another example, methods include: 1) affixing an asymmetric polygonal cover bar to the distal end of an optical detector scatter cap assembly; 2) detecting and measuring light (e.g., fluorescence, forward-scattered light, side-scattered light, etc.) from the sample; 3) removing the asymmetric polygonal cover bar; and 4) affixing a rectangular cover bar to the distal end of the optical detector scatter cap assembly.

In another example, methods include: 1) affixing a curvilinear cover bar to the distal end of an optical detector scatter cap assembly; 2) detecting and measuring light (e.g., fluorescence, forward-scattered light, side-scattered light, etc.) from the sample; 3) removing the curvilinear cover bar; and 4) affixing an asymmetric polygonal cover bar to the distal end of the optical detector scatter cap assembly.

In another example, methods include: 1) affixing an asymmetric polygonal cover bar to the distal end of an optical detector scatter cap assembly; 2) detecting and measuring light (e.g., fluorescence, forward-scattered light, side-scattered light, etc.) from the sample; 3) removing the asymmetric polygonal cover bar; and 4) affixing a curvilinear cover bar to the distal end of the optical detector scatter cap assembly.

In practicing the subject methods according to certain embodiments, the first cover bar may be removed and replaced with the second cover bar to reduce the signal-to-noise ratio of the detector signal that is measured during irradiation of the sample. In these embodiments, methods include monitoring the detector signal intensity during irradiation of the sample to assess the signal-to-noise ratio of the detector signal. In some instances, monitoring includes collecting real-time data from the detector or assessing the detector signal at regular intervals such as every 0.001 milliseconds, every 0.01 milliseconds, every 0.1 milliseconds, every 1 millisecond, every 5 milliseconds, every 10 milliseconds, every 100 milliseconds, including every 1000 milliseconds or some other interval.

Where the assessed signal-to-noise ratio of the detector signal indicates that a particular cover bar provides for a signal-to-noise ratio that is less than optimal, methods include removing the first cover bar and affixing a second cover bar to the optical detector scatter cap assembly and subsequently monitoring the signal intensity. Depending on the type of light from the sample being detected (e.g., fluorescence, forward-scattered light, side-scattered light, etc.) and the desired reduction in signal-to-noise ratio of the detector signal, the first cover cover bar may be replaced by a second cover bar having a different shape, a different size or a combination thereof as noted above.

Kits

Aspects of the invention further include kits, where kits include one or more optical detector scatter cap assemblies and cover bars as described herein. In some instances, the kits may include a single optical detector scatter cap and two or more, including three or more, four or more, five or more, etc., cover bars, which may be mated with and removed from the optical detector scatter cap as described above. In some embodiments, the plurality of cover bars may have the same or different dimensions, e.g., the two or more scatter bars may differ from each other in terms of width. In other embodiments, the cover bars may have different shapes, such as a rectangular, curvilinear or irregular, asymmetric polygonal shapes.

Kits according to certain embodiments include two or more optical detector scatter caps that are configured for coupling to two different types of detectors (e.g., fluorescence detectors, side scatter detectors, forward scatter detectors, etc.). In some instances, the optical detector scatter cap housings have different dimensions. In other instances, the optical detector scatter cap may include different types of fasteners for coupling to a detector. For example, kits may include a first optical detector scatter cap that includes one or more grooves, notches or protrusions for coupling to a detector and a second optical detector scatter cap that includes a screw thread configured to be screw threaded with a detector. In still other instances, the optical detector scatter caps may include different types of aligners or fasteners for mating with a cover bar. For example, kits may include a first optical detector scatter cap that includes magnets for aligning and mating with the cover bar and a second optical detector scatter cap that includes brackets for aligning and mating with the cover bar.

Where desired, the kits can include one or more assay components (e.g., labeled reagents, buffers, etc., such as described above). In some instances, the kits may further include a sample collection device, e.g., a lance or needle configured to prick skin to obtain a whole blood sample, a pipette, etc., as desired.

The various assay components of the kits may be present in separate containers, or some or all of them may be pre-combined. For example, in some instances, one or more components of the kit, e.g., one or more optical detector scatter caps and/or cover bars, are present in a sealed pouch, e.g., a sterile foil pouch or envelope.

In addition to the above components, the subject kits may further include, in certain embodiments, instructions for practicing the subject methods. The instructions may include directions and parameters for each scatter bar based on shape and size. In certain embodiments, the instructions include directions for choosing a particular shape of cover bar based on sample characteristics (e.g., particle types, sizes, etc.) as well as on the properties of the irradiating light source (e.g., wavelength of light, beam profile, irradiation spot size). In other embodiments, instructions include directions for choosing a particular size of cover bar based on sample characteristics (e.g., particle types, sizes, etc.) as well as on the properties of the irradiating light source (e.g., wavelength of light, beam profile, irradiation spot size).

Instructions in the subject kits may be provided in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject optical detector scatter cap assembly find use in a variety of applications. In certain embodiments, the optical detector scatter cap assembly finds use in enhancing measurements of light from a sample (e.g., fluorescence or scattered light from a sample in a flow stream of a flow cytometer). Embodiments of the present disclosure find use where enhancing the effectiveness of emission and scattered light measurements in flow cytometry are desired, such as in research and high throughput laboratory testing. The present disclosure also finds use where it is desirable to provide a flow cytometer with improved cell sorting accuracy, enhanced particle collection, reduced energy consumption, particle charging efficiency, more accurate particle charging and enhanced particle deflection during cell sorting.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Notwithstanding the appended clauses, the disclosure set forth herein is also defined by the following clauses:

1. An optical detector scatter cap assembly, the assembly comprising:
    a housing comprising a proximal end and a distal end;
    an orifice at the distal end of the housing;
    a scatter bar affixed to the housing and extending across the orifice; and
    a cover bar that is configured to be reversibly mated with the scatter bar,
    wherein the cover bar has a width that is equal to or greater than the scatter bar.
2. The scatter cap assembly according to clause 1, wherein the housing comprises an aligner that positions the cover bar to be parallel with the scatter bar.
3. The scatter cap assembly according to any one of clauses 1-2, wherein the housing comprises a fastener for reversibly immobilizing the cover bar to the scatter bar.
4. The scatter cap assembly according to any one of clauses 1-3, wherein the scatter bar has a width from 0.1 mm to 1.5 mm.
5. The scatter cap assembly according to any one of clauses 1-4, wherein the cover bar has a width from 2 mm to 6 mm.
6. The scatter cap assembly according to any one of clauses 1-5, wherein the cover bar is rectangular.
7. The scatter cap assembly according to any one of clauses 1-5, wherein the cover bar is semi-circular.
8. The scatter cap assembly according to any one of clauses 1-5, wherein the cover bar is asymmetric polygonal.
9. The scatter cap assembly according to clause 8, wherein the asymmetric polygonal cover bar has a width at a first end of 2 mm and a width at a second end of from 4 to 5 mm.
10. The scatter cap assembly according to any one of clauses 1-9, wherein cover bar comprises a magnetic material.
11. The scatter cap assembly according to clause 10, wherein the cover bar comprises an oxide-coated magnetic steel.
12. A method for comprising affixing a cover bar to a distal end of an optical detector scatter cap, wherein the optical detector scatter cap comprises:
    a housing comprising a proximal end and a distal end;
    an orifice at the distal end of the housing; and
    a scatter bar affixed to the distal end of the housing and extending across the orifice,
    wherein the cover bar has a width that is equal to or greater than the scatter bar.
13. The method according to clause 12, wherein the method comprises:
    affixing a first cover bar to the distal end of the optical detector scatter cap;
    removing the first cover bar; and
    affixing a second cover bar to the distal end of the optical detector scatter cap.
14. The method according to clause 13, wherein the first cover bar has a width that is greater than the width of the second cover bar.
15. The method according to clause 13, wherein the first cover bar has a width that is less than the width of the second cover bar.
16. The method according to any one of clauses 13-15, wherein the first cover bar is rectangular.
17. The method according to any one of clauses 13-15, wherein the second cover bar is asymmetric polygonal.
18. The method according to any one of clauses 12-17, wherein the housing comprises an aligner that positions the cover bar to be parallel with the scatter bar at the distal end of the housing.
19. The method according to any one of clauses 12-18, wherein the housing comprises a fastener for immobilizing the cover bar to the scatter bar.
20. The method according to any one of clauses 12-19, wherein the scatter bar has a width from 0.1 mm to 1.5 mm.
21. The method according to clause 20, wherein the cover bar has a width from 2 mm to 6 mm.
22. The method according to any one of clauses 12-21, wherein the cover bar is rectangular.
23. The method according to any one of clauses 12-21, wherein the cover bar is semi-circular.
24. The method according to any one of clauses 12-21, wherein the cover bar is asymmetric polygonal.
25. The method according to clause 24, wherein the asymmetric polygonal cover bar has a width at a first end of 2 mm and a width at a second end of from 4 to 5 mm.
26. The method according to any one of clauses 12-25, wherein cover bar comprises a magnetic material.
27. The method according to any one of clauses 12-26, wherein the cover bar comprises an oxide-coated magnetic steel.
28. A kit comprising:
    an optical detector scatter cap comprising:
    a housing comprising a proximal end and a distal end;
    an orifice at the distal end of the housing;
    a scatter bar affixed to the housing and extending across the orifice; and
    two or more cover bars that are configured to be reversibly mated with the scatter bar.
29. The kit according to clause 28, wherein the housing comprises an aligner that positions the cover bar to be parallel with the scatter bar.
30. The kit according to any one of clauses 28-29, wherein the housing comprises a fastener for immobilizing the cover bar to the scatter bar.
31. The kit according to any one of clauses 28-30, wherein the scatter bar has a width from 0.1 mm to 1.5 mm.
32. The kit according to clause 31, wherein each cover bar has a width from 2 mm to 6 mm.
33. The kit according to any one of clauses 28-32, wherein each cover bar has a shape selected from the group consisting of rectangular, semicircular and asymmetric polygonal.
34. The kit according to clause 33, wherein at least one cover bar is rectangular.
35. The kit according to clause 33, wherein at least one cover bar is curvilinear.

36. The kit according to clause 33, wherein at least one cover bar is asymmetric polygonal.
37. The kit according to clause 36, wherein the asymmetric polygonal cover bar has a width at a first end of 2 mm and a width at a second end of from 4 to 5 mm.
38. The kit according to any one of clauses 28-37, wherein each cover bar comprises a magnetic material.
39. The kit according to any one of clauses 28-37, wherein each cover bar comprises an oxide-coated magnetic steel.
40. The kit according to any one of clauses 28-39, wherein the kit comprises two or more cover bars in a container.
41. The kit according to clause 40, wherein the container is a pouch.
42. The kit according to any one of clauses 28-41, wherein the kit comprises two or more optical detector scatter caps.
43. The kit according to clause 42, wherein each optical detector scatter cap comprises different fasteners for reversibly mating the cover bar with the scatter bar.
44. The kit according to any one of clauses 42-43, wherein the housing of each optical detector scatter cap comprises an orifice having a different size.
45. A system comprising:
   a detector; and
   an optical detector scatter cap assembly, the assembly comprising:
      a housing comprising a proximal end and a distal end;
      an orifice at the distal end of the housing;
      a scatter bar affixed to the housing and extending across the orifice; and
      a cover bar that is configured to be reversibly mated with the scatter bar,
   wherein the cover bar has a width that is equal to or greater than the scatter bar.
46. The system according to clause 45, wherein the detector is positioned to detect scattered light from a flow stream.
47. The system according to clause 46, wherein the detector is positioned to detect forward-scattered light.
48. The system according to clause 46, wherein the detector is positioned to detect side-scattered light.
49. The system according to any one of clauses 45-48, wherein the detector comprises a position sensing detector.
50. The system according to clause 49, wherein the detector comprises a quadrant photodiode.
51. The system according to any one of clauses 45-48, wherein the detector comprises a photodiode array.
52. The system according to clause 51, wherein the photodiode array comprises two or more photodiode detectors.
53. The system according to any one of clauses 45-52, further comprising an optical adjustment component positioned between the proximal end of the optical detector scatter cap assembly housing and the detector.
54. The system according to clause 53, wherein the optical adjustment component comprises a focusing lens.
55. The system according to clause 53, wherein the optical adjustment component comprises a de-magnifying lens.
56. The system according to clause 53, wherein the optical adjustment component comprises a collimating lens.
57. The system according to clause 53, wherein the optical adjustment component comprises a wavelength separator.
58. The system according to clause 57, wherein the wavelength separator comprises a cutoff filter lens.
59. The system according to any one of clauses 45-58, further comprising a light source.
60. The system according to clause 59, wherein the light source comprises a laser.
61. The system according to any one of clauses 45-60, wherein the housing comprises an aligner that positions the cover bar to be parallel with the scatter bar.
62. The system according to any of clauses 45-61, wherein the housing comprises a fastener for immobilizing the cover bar to the scatter bar.
63. The system according to any one of clauses 45-62, wherein the scatter bar has a width from 0.1 mm to 1.5 mm.
64. The system according to any one of clauses 45-63, wherein the cover bar has a width from 2 mm to 6 mm.
65. The system according to any one of clauses 45-64, wherein the cover bar is rectangular.
66. The system according to any one of clauses 45-64, wherein the cover bar is semi-circular.
67. The system according to any one of clauses 45-63, wherein the cover bar is asymmetric polygonal.
68. The system according to clause 67, wherein the asymmetric polygonal cover bar has a width at a first end of 2 mm and a width at a second end of from 4 to 5 mm.
69. The system according to any one of clauses 45-68, wherein cover bar comprises a magnetic material.
70. The system according to any one of clauses 45-69, wherein the cover bar comprises an oxide-coated magnetic steel.
71. The system according to any one of clauses 45-70, wherein the system is a flow cytometer.
72. A method comprising:
   affixing an optical detector scatter cap to a detector, the optical detector scatter cap comprising:
      a housing comprising a proximal end and a distal end;
      an orifice at the distal end of the housing;
      a scatter bar extending across the orifice, wherein the scatter bar is configured for reversibly immobilizing a cover bar having a width equal to or greater than the scatter bar;
   irradiating a sample comprising cells with a light source;
   detecting light scattered by the sample with the detector; and
   measuring the detected light at one or more wavelengths.
73. The method according to clause 72, wherein the width of the cover bar is greater than 2 mm when the cells in the sample have a size that is less than 4 times the wavelength of the light source.
74. The method according to clause 72, wherein the width of the cover bar is 2 mm or less when the cells in the sample have a size that is 4 times the wavelength of the light source or greater.
75. The method according to any one of clauses 73-74, further comprising determining the size of cells in the sample.
76. The method according to any one of clauses 72-75, further comprising removing the cover bar from the optical detector scatter cap and reversibly mating a second cover bar with the scatter bar.
77. The method according to clause 76, wherein the second cover bar has a different width from the first cover bar.
78. The method according to any one of clauses 76-77, wherein the second cover bar has a different shape from the first cover bar.
79. The method according to any one of clauses 72-78, wherein the housing comprises an aligner that positions the cover bar to be parallel with the scatter bar.
80. The method according to any one of clauses 72-79, wherein the housing comprises a fastener for immobilizing the cover bar to the scatter bar.

81. The method according to any one of clauses 72-80, wherein the scatter bar has a width from 0.1 mm to 1.5 mm.
82. The method according to any one of clauses 72-81, wherein the cover bar has a width from 2 mm to 6 mm.
83. The method according to any one of clauses 72-80, wherein the cover bar is rectangular.
84. The method according to any one of clauses 72-80, wherein the cover bar is semi-circular.
85. The method according to any one of clauses 72-80, wherein the cover bar is asymmetric.
86. The method according to clause 85, wherein the cover bar has a width at a first end of 2 mm and a width at a second end of from 4 to 5 mm.
87. The method according to any one of clauses 72-86, wherein cover bar comprises a magnetic material.
88. The method according to any one of clauses 72-86, wherein the cover bar comprises an oxide-coated magnetic steel.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An optical detector scatter cap assembly, the assembly comprising:
    a housing comprising a proximal end and a distal end;
    an orifice at the distal end of the housing;
    a scatter bar affixed to the housing and extending across the orifice; and
    a cover bar that is configured to be reversibly mated with the scatter bar,
    wherein the cover bar has a width that is equal to or greater than the scatter bar.
2. The scatter cap assembly according to claim 1, wherein the housing comprises an aligner that positions the cover bar to be parallel with the scatter bar.
3. The scatter cap assembly according to claim 1, wherein the housing comprises a fastener for reversibly immobilizing the cover bar to the scatter bar.
4. The scatter cap assembly according to claim 1, wherein the scatter bar has a width from 0.1 mm to 1.5 mm.
5. The scatter cap assembly according to claim 1, wherein the cover bar has a width from 2 mm to 6 mm.
6. The scatter cap assembly according to claim 1, wherein the cover bar is rectangular.
7. The scatter cap assembly according to claim 1, wherein the cover bar is semi-circular.
8. The scatter cap assembly according to claim 1, wherein the cover bar is asymmetric polygonal.
9. The scatter cap assembly according to claim 8, wherein the asymmetric polygonal cover bar has a width at a first end of 2 mm and a width at a second end of from 4 to 5 mm.
10. The scatter cap assembly according to claim 1, wherein cover bar comprises a magnetic material.
11. The scatter cap assembly according to claim 10, wherein the cover bar comprises an oxide-coated magnetic steel.
12. A method comprising affixing a cover bar to a distal end of an optical detector scatter cap, wherein the optical detector scatter cap comprises:
    a housing comprising a proximal end and a distal end;
    an orifice at the distal end of the housing; and
    a scatter bar affixed to the distal end of the housing and extending across the orifice,
    wherein the cover bar has a width that is equal to or greater than the scatter bar.
13. The method according to claim 12, wherein the method comprises:
    affixing a first cover bar to the distal end of the optical detector scatter cap;
    removing the first cover bar; and
    affixing a second cover bar to the distal end of the optical detector scatter cap.
14. The method according to claim 13, wherein the first cover bar has a width that is greater than the width of the second cover bar.
15. The method according to claim 13, wherein the first cover bar has a width that is less than the width of the second cover bar.
16. The method according to claim 13, wherein the housing comprises an aligner that positions the cover bar to be parallel with the scatter bar at the distal end of the housing.
17. The method according to claim 13, wherein the housing comprises a fastener for immobilizing the cover bar to the scatter bar.
18. The method according to claim 12, wherein cover bar comprises a magnetic material.
19. The method according to claim 12, the method further comprising:
    irradiating a sample comprising cells with a light source;
    detecting light scattered by the sample with the detector; and
    measuring the detected light at one or more wavelengths.
20. A kit comprising:
    an optical detector scatter cap comprising:
        a housing comprising a proximal end and a distal end;
        an orifice at the distal end of the housing;
        a scatter bar affixed to the housing and extending across the orifice; and
    two or more cover bars that are configured to be reversibly mated with the scatter bar.

* * * * *